US00PP13390P2

(12) United States Plant Patent
Klemm

(10) Patent No.: US PP13,390 P2
(45) Date of Patent: Dec. 17, 2002

(54) GERANIUM PLANT NAMED 'KLEROPUR'

(75) Inventor: Nils Klemm, Stuttgart (DE)

(73) Assignee: Klemm + Sohn GmbH + Co. KG, Stuttgart (DE)

( * ) Notice: Subject to any disclaimer, the term of this patent is extended or adjusted under 35 U.S.C. 154(b) by 2 days.

(21) Appl. No.: 09/876,937

(22) Filed: Jun. 11, 2001

(51) Int. Cl.[7] ..... A01H 5/00

(52) U.S. Cl. ..... Plt./332

(58) Field of Search ..... Plt./332, 324

*Primary Examiner*—Bruce R. Campell
*Assistant Examiner*—June Hwu
(74) *Attorney, Agent, or Firm*—C. A. Whealy

(57) ABSTRACT

A new and distinct cultivar of Ivy Geranium plant named 'Kleropur', characterized by its uniform and cascading growth habit; green-colored leaves with darker green zonation pattern; and purple-colored double flowers.

1 Drawing Sheet

BOTANICAL CLASSIFICATION/CULTIVAR DESIGNATION

*Pelargonium peltatum* cultivar Kleropur.

BACKGROUND OF THE INVENTION

The present invention relates to a new and distinct cultivar of Ivy Geranium plant, botanically known as *Pelargonium peltatum*, and hereinafter referred to by the name 'Kleropur'.

The new Ivy Geranium is a product of a planned breeding program conducted by the Inventor in Stuttgart, Germany. The objective of the breeding program was to develop new Ivy Geraniums with uniform growth habit and interesting flower and foliage colors.

The new Ivy Geranium originated from a cross made by the Inventor in August, 1994 of two unidentified proprietary selections of *Pelargonium peltatum*, not patented. The cultivar Kleropur was discovered and selected by the Inventor as a flowering plant within the progeny from this cross in a controlled environment in Stuttgart, Germany, in September, 1995.

Asexual reproduction of the new cultivar by terminal cuttings taken at Stuttgart, Germany, since November, 1995, has shown that the unique features of this new Ivy Geranium are stable and reproduced true to type in successive generations of asexual reproduction.

SUMMARY OF THE INVENTION

The following traits have been repeatedly observed and are determined to be the unique characteristics of 'Kleropur'. These characteristics in combination distinguish 'Kleropur' as a new cultivar and distinguish it from other known Ivy Geranium cultivars:

1. Uniform and cascading growth habit.

2. Green-colored leaves with darker green zonation pattern.

3. Purple-colored double flowers.

Plants of the new Ivy Geranium differ primarily from plants of the parent selections in plant growth habit, leaf color and flower color.

BRIEF DESCRIPTION OF THE PHOTOGRAPH

The accompanying colored photograph illustrates the overall appearance of the new cultivar, showing the colors as true as it is reasonably possible to obtain in colored reproductions of this type. The photograph comprises a side perspective view of four typical flowering plants of 'Kleropur' that were grown for about three months in a hanging basket container. Flower and foliage colors in the photograph may differ slightly from the color values cited in the detailed botanical description which accurately describe the colors of the new Ivy Geranium.

DETAILED BOTANICAL DESCRIPTION

The cultivar Kleropur has not been observed under all possible environmental conditions. The phenotype may vary somewhat with variations in environment, such as temperature and light intensity, without, however, any variance in genotype. The following observations, measurements and comparisons describe plants that were planted in January in 12-cm pots in Stuttgart, Germany, pinched one time about two weeks later, and grown for about three months under commercial practice in a glass-covered greenhouse with day temperatures about 18 to 22° C., night temperatures about 15 to 18° C. and light levels about 20,000 to 50,000 lux. In the following description, color references are made to The Royal Horticultural Society Colour Chart except where general terms of ordinary dictionary significance are used.

Botanical classification: *Pelargonium peltatum* cultivar Kleropur.

Parentage:

*Female parent.*—Unidentified proprietary selection of *Pelargonium peltatum*, not patented.

*Male parent.*—Unidentified proprietary selection of *Pelargonium peltatum*, not patented.

Propagation:

*Type cutting.*—Terminal cuttings.

*Time to initiate roots.*—Summer and winter: About 10 days at 20 to 22° C.

*Time to develop roots.*—Summer: About 18 days at 22° C. Winter: About 20 days at 20° C.

*Root description.*—Fibrous, freely branching, and white in color.

Plant description:

*General appearance.*—Initially upright, then cascading growth habit; uniform; densely foliated.

*Crop time.*—About three months are required to produced a finished flowering plant in 12-cm container.

*Growth and branching habit.*—Vigorous and freely basal branching; about four to five lateral branches develop after pinching, that is, removal of terminal apices.

*Plant height* (*to top of flower umbels*).—About 27.5 cm.

*Plant height* (*to top of foliar plane*).—About 23.5 cm.

*Plant width.*—About 26 cm.

*Lateral branches.*—Length: About 8.5 cm. Internode length: About 2 to 3 cm. Texture: Slightly pubescent. Color: 143C.

*Foliage description.*—Leaves simple, generally symmetrical, alternate arrangement. Quantity of leaves per lateral branch: About 5 to 6. Length, mature leaves: About 6.5 cm. Width, mature leaves: About 8.5 cm. Shape: Reniform with lobing, ivy shaped. Apex: Acute. Base: Lobed, overlapping. Margin: Entire. Venation pattern: Palmate. Texture: Upper surface: Slightly pubescent, rough and leathery. Lower surface: Glabrous, rough and leathery. Color: Young foliage, upper surface: 146A; zonation pattern, 147A in color. Young foliage, lower surface: 143C. Mature foliage, upper surface: 137B; zonation pattern, 147A in color, located about 2.5 cm from the margin, and about 6 mm in width. Mature foliage, lower surface: 137C. Venation, upper surface: 137C. Venation, lower surface: 143C. Petiole: Length: About 6 cm. Diameter: About 2 mm. Texture, both surfaces: Smooth. Color, both surfaces: 138B.

Flower description:

*Flower arrangement and type.*—Purple-colored flowers arranged in flat hemispherical umbels arising from apical leaf axils. Umbels displayed above the foliage. Freely flowering; at full flowering about 6 to 8 open umbels and about 3 to 5 developing umbels per plant. Flowers double in form, rounded and mostly flat. Flowers last about 3 to 5 days on the plant. Umbels persistent, flowers not persistent. Flowers not fragrant.

*Flowering season.*—Year-round under greenhouse conditions. In the garden, flowering is continuous from spring until fall.

*Umbels*—Height: About 6 to 8 cm. Diameter: About 10 to 14 cm. Number of flowers and flower buds per umbel: About 10 to 15. Flower diameter: About 4.25 cm. Flower depth (height): About 1 cm.

*Flower buds.*—Length: About 1 cm. Diameter: About 6 mm. Shape: Elliptic. Color: 139C.

*Petals.*—Quantity: About 8 to 12 per flower arranged in about two whorls. Length, outer petals: About 2.5 cm. Width, outer petals: About 1 cm. Shape: Ovate. Apex: Rounded. Base: Attenuate. Margin: Entire. Texture, both surfaces: Smooth, velvety. Color: When opening and fully opened, upper surface: 74B; color does not fade with subsequent development. When opening and fully opened, lower surface: 72C. Venation, both surfaces: 74B.

*Petaloids.*—Quantity: About 2 to 5 per flower. Length: About 4 to 11 mm; irregular in size. Width: About 2 to 6 mm; irregular in size. Shape: Variable, irregular. Apex: Mostly rounded. Base: Attenuate. Margin: Mostly entire. Texture, both surfaces: Smooth, velvety. Color: When opening and fully opened, upper surface: 74B; towards base, 74C; color does not fade with subsequent development. When opening and fully opened, lower surface: 72C; towards base, 74C. Venation, upper surface: 74A. Venation, lower surface: 72A.

*Sepals.*—Quantity: Five, arranged in a single whorl. Length: About 1.1 cm. Width: About 5 mm. Shape: Elliptic. Apex: Narrowly acute. Margin: Entire. Texture, both surfaces: Pubescent, velvety. Color, upper and lower surfaces: 148A.

*Peduncle* (*umbel stem*).—Length: About 7 to 12 cm. Diameter: About 2 mm. Angle: Erect to slightly bent. Strength: Strong. Texture: Slightly pubescent. Color: 139C.

*Pedicel* (*individual flower stem*).—Length: About 1.7 cm. Diameter: About 2 mm. Angle: Erect. Strength: Strong. Texture: Slightly pubescent. Color: 139C.

*Reproductive organs.*—Androecium: Anther quantity: Five per flower. Anther length: About 2 mm. Anther shape: Ovate. Anther color: 33C. Pollen amount: Moderate. Pollen color: 33B. Gynoecium: Pistil quantity: One per flower. Pistil length: About 9 mm. Stigma shape: Five-parted, star-shaped. Stigma color: 72C. Style length: About 5 mm. Style color: 149C. Ovary color: 138C.

*Seed.*—Length: About 4 to 5 mm. Diameter: About 1.5 to 2 mm. Shape: Ovoid. Color: Brownish.

Disease tolerance: Plants of the new Ivy Geranium have been shown to be tolerant to pathogens common to Pelargonium, such as Botrytis.

Weather tolerance: Plants of the new Ivy Geranium have been observed to tolerate rain and temperatures from 8 to 35° C.

It is claimed:

1. A new and distinct cultivar of Ivy Geranium plant named 'Kleropur', as herein illustrated and described.

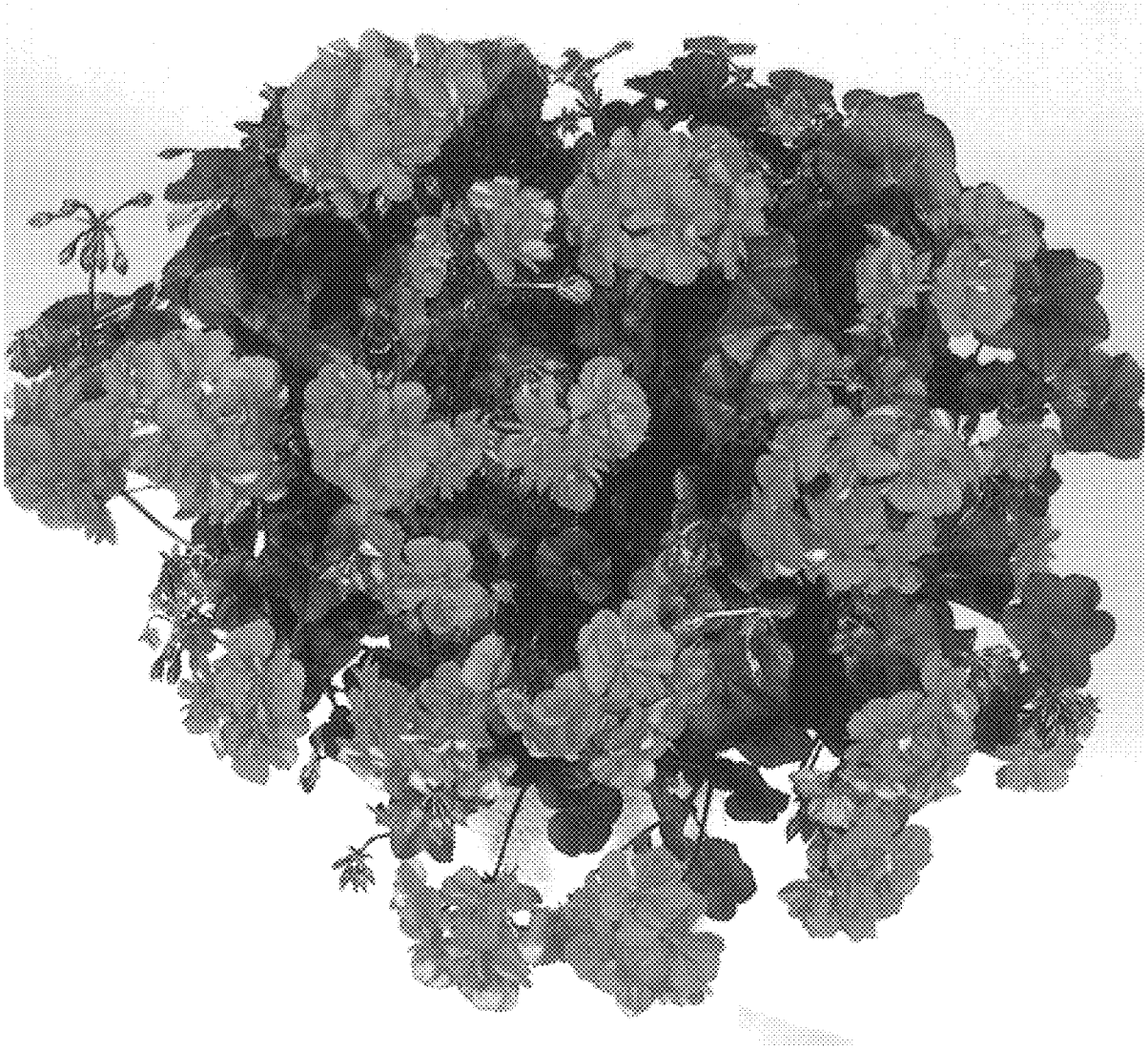

* * * * *